US012582628B2

(12) United States Patent
Dinarello et al.

(10) Patent No.: US 12,582,628 B2
(45) Date of Patent: Mar. 24, 2026

(54) METHODS FOR TREATING BREAST CANCER

(71) Applicant: Olatec Therapeutics, Inc., New York, NY (US)

(72) Inventors: Charles A. Dinarello, Boulder, CO (US); Isak Tengesdal, Denver, CO (US)

(73) Assignee: OLATEC THERAPEUTICS, INC., New York, NY (US)

( * ) Notice: Subject to any disclaimer, the term of this patent is extended or adjusted under 35 U.S.C. 154(b) by 807 days.

(21) Appl. No.: 17/659,121

(22) Filed: Apr. 13, 2022

(65) Prior Publication Data

US 2022/0249425 A1 Aug. 11, 2022

Related U.S. Application Data

(63) Continuation of application No. PCT/US2020/055219, filed on Oct. 12, 2020.

(60) Provisional application No. 62/914,833, filed on Oct. 14, 2019.

(51) Int. Cl.
*A61K 31/275* (2006.01)
*A61K 39/395* (2006.01)
*A61P 35/00* (2006.01)

(52) U.S. Cl.
CPC ........ *A61K 31/275* (2013.01); *A61K 39/3955* (2013.01); *A61P 35/00* (2018.01)

(58) Field of Classification Search
CPC .... A61K 31/275; A61K 39/3955; A61P 35/00
See application file for complete search history.

(56) References Cited

U.S. PATENT DOCUMENTS

| | | | | |
|---|---|---|---|---|
| 9,815,898 | B2 * | 11/2017 | Freeman | A61P 35/04 |
| 10,500,184 | B2 | 12/2019 | St. Laurent | |
| 11,576,888 | B2 | 2/2023 | Marchetti et al. | |

FOREIGN PATENT DOCUMENTS

| | | | |
|---|---|---|---|
| CN | 104768553 | A | 7/2015 |
| WO | 2012082718 | A2 | 6/2012 |
| WO | 2018129231 | A1 | 7/2018 |
| WO | 2018129347 | A1 | 7/2018 |
| WO | 2019152627 | A1 | 7/2018 |
| WO | 2019032672 | A1 | 2/2019 |
| WO | 2019182981 | A1 | 9/2019 |

OTHER PUBLICATIONS

Marchetti, OLT1177, a β-sulfonyl nitrile compound, safe in humans, inhibits the NLRP3 inflammasome and reverses the metabolic cost of inflammation, Proc. Natl. Acad. Sci. U.S.A. 115 (7) E1530-E1539 (Year: 2018).*

Tulotta, C., et al. The role of IL-1B in breast cancer bone metastasis. Endocrine-Related Cancer, 25(7), R421-R434. (Year: 2018).*

Pensa, S., Stat3 and the Inflammation/Acute Phase Response in Involution and Breast Cancer J Mammary Gland Biol Neoplasia (2009) 14:121-129 (Year: 2009).*

Marchetti et al, OLT1177,aB-sulfonylnitrile compound, safe in humans, inhibits the NLRP3 inflammasome and reverses the metabolic cost of inflammation, Proc. Natl. Acad. Sci. U.S.A. 115(7)E1530-E1539 (Year: 2018).*

Marchetti, Carlo et al., "OLT1177, a β-sulfonyl nitrile compound, safe in humans, inhibits the NLRP3 inflammasome and reverses the metabolic cost of inflammation," Jan. 29, 2018, www.pnas.org/cgi/doi/10.1073/pnas. 1716095115.

Kaplanov et al. "Blocking IL-113 Reverses the Immunosuppression in Mouse Breast Cancer and Synergizes with anti-PD-1 for Tumor Abrogation," Proceedings of the National Academy of Sciences of the United States of America, Jan. 22, 2019 (Jan. 22, 2019), vol. 116, Iss. 4, pp. 1361-1369.

United States Patent & Trademark Office (USPTO), International Search Report and Written Opinion, PCT/US2020/8055219, Jan. 19, 2021.

European Patent Office (EPO), Extended European Search Report, EP No. 20877745.8, Oct. 17, 2023, corresponding to U.S. Appl. No. 17/659,121.

Ershaid, Nour et al., NLRP3 inflammasome in fibroblasts links tissue damage with inflammation in breast cancer progression and metastasis, Nature Communications, Dec. 16, 2018, pp. 1-15, Spring Nature.

Kolb, Ryan et al., Inflammasomes in cancer: a doubled-edged sword, Protein & Cell, Jun. 23, 2013, pp. 1-20, Springer.

Castaño, Zafira et al., IL-1β inflammatory response driven by primary breast cancer prevents metastasis-initiating cell colonization, Nature Cell Biology, Mar. 21, 2017, pp. 1084-1097, vol. 20, Springer.

Tengesdal, Isak W. et al., Activation of Host-NLRP3 Inflammasome in Myeloid Cells Dictates Response to Anti-PD-1 Therapy in Metastatic Breast Cancers, pharmaceuticals, Feb. 22, 2022, vol. 15, issue 5, MDPI Open Access Journals.

* cited by examiner

*Primary Examiner* — Adam C Milligan
*Assistant Examiner* — Ernesto Valle
(74) *Attorney, Agent, or Firm* — PERKINS COIE LLP; Viola T. Kung

(57) ABSTRACT

The present invention is directed to a method of treating breast cancer. The method comprises administering to a subject in need thereof an effective amount of dapansutrile, or a pharmaceutically acceptable solvate thereof. The method optionally comprises further administering to the subject an effective amount of a checkpoint inhibitor.

7 Claims, 12 Drawing Sheets

Specification includes a Sequence Listing.

METHODS FOR TREATING BREAST CANCER

This application is a continuation of PCT/US2020/055219, filed Oct. 12, 2020; which claims the benefit of U.S. Provisional Application Nos. 62/914,833, filed Oct. 14, 2019. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Oct. 6, 2020, and a size of 1.31 kilobytes. The Sequence Listing filed via EFS-Web is part of the specification and is hereby incorporated in its entirety by reference herein.

TECHNICAL FIELD

The present invention relates to methods for treating breast cancer by administering an effective amount of dapansutrile.

BACKGROUND

Tumorigenesis is initiated by genomic alterations including point mutations, gene deletion, chromosomal rearrangements leading to cell transformation, self-sufficient proliferation, insensitivity to anti-proliferative signals, evasion of apoptosis and unlimited replicative potential, leading ultimately to tissue invasion and metastasis. However, expansion of tumor cells is linked to a complex network of events that involve both cancer and non-cancer cells. Chronic inflammation is a classic example of such promoting conditions (1, 2).

The pro-inflammatory cytokine IL-1β is a potent mediator of many chronic inflammatory diseases (3). Consistent with the linkage of cancer to chronic inflammation, it has been shown that IL-1β is over-expressed in several tumors and functions as an inducer of tumor promoting mechanisms including angiogenesis, immunosuppression, recruitment of tumor-associated macrophages (TAMs) and metastasis (4-6).

Types of breast cancer include ductal carcinoma in situ (DCIS), invasive ductal carcinoma (IDC), triple negative breast cancer (TNBC), inflammatory breast cancer (IBC), metastatic breast cancer, and breast cancer during pregnancy, among other types. Triple negative breast cancer tumors are characterized by an absence of estrogen receptors (ER), progesterone receptors (PR), and elevated human epidermal growth factor receptor 2 (HER2) protein levels (7).

NLRP3 (NOD-like receptor family, pyrin domain containing 3), also known as NLRP3 or cryopyrin, is one of the sensors of the inflammasome, a macromolecular structure involved in interleukin-1β (IL-1β) and IL-18 processing. NLRP3 senses intracellular danger during intracellular infections (bacterial and viral proteins) or tissue injury (ischemia). NLRP3 activation leads to recruitment of ASC (apoptosis-associated speck-like protein containing carboxyterminal caspase recruitment domain) and caspase-1 leading to inflammasome formation and ultimately cell death.

Dapansutrile is a small, synthetic molecule of β-sulfonyl nitrile which has been demonstrated to selectively inhibit the NLRP3 inflammasome and be safe when orally administered to healthy subjects (8).

There is a need for a method for treating breast cancer. The method should be effective and have no significant side effects.

BRIEF DESCRIPTION OF THE DRAWINGS

FIG. 1A depicts a schematic overview of experimental design. FIG. 1B depicts a chart showing tumor volume in mice treated with dapansutrile (OLT1177®) compared to vehicle. Measurements were taken following tumor resection. $^{}p<0.01$ (n=5). FIG. 1C depicts a growth curve showing tumor volume in mice treated with dapansutrile compared with tumors in mice fed a standard diet. Measurements were taken from live mice on days as indicated. FIG. 1C (n=5). FIG. 1**D depicts a chart showing percent survival in mice fed a dapansutrile-enriched (OLT1177®) diet. $^{*}p<0.05$.

FIG. 2A depicts a schematic overview of experimental design. FIG. 2B depicts a chart of tumor volume analysis showing that tumor volume is reduced in mice treated with dapansutrile (OLT1177) and mice treated with dapansutrile and anti-IL1α. FIG. 2C depicts a growth curve showing that tumors in mice treated with dapansutrile compared to mice treated with a vehicle control. Measurements were taken from live mice on days as indicated. FIG. 2C (n=5). FIGS. 2D and 2E depict charts showing relative mRNA expression levels of TSLP (FIG. 2D) and its associated receptor (TSLPR; FIG. 2E) in primary 4T1 tumors from mice treated with dapansutrile compared to mice treated with a vehicle control. $^{*}p<0.05$ (n=8, two independent experiments). FIGS. 2F and 2G depict charts showing relative mRNA expression of TSLP (FIG. 2F) and TSLPR (FIG. 2G) in vitro using the human TNBC cell line MDA-468. Cells were stimulated with IL-la and treated with dapansutrile as indicated. $^{*}p<0.05$ (n=8, two independent experiments).

FIG. 3A depicts a schematic overview of experimental design. FIG. 3B depicts a chart showing tumor volume in 4T1 TNBC mice treated with dapansutrile (OLT1177®), anti-PD-1, both anti-PD-1 and dapansutrile, or vehicle. Measurements were taken following tumor resection. FIG. 3B (vehicle vs. anti-PD-1, p=0.0069; vehicle vs. dapansutrile, p=0.0041; vehicle vs. dapansutrile+anti-PD-1, p=0.0014) (n=5). FIG. 3C depicts a growth curve showing tumor volume over 15 days in mice treated with anti-PD-1, dapansutrile, both anti-PD-1 and dapansutrile, or vehicle. Measurements were taken from live mice on days as indicated. FIG. 3C (n=5). FIG. 3D depicts a chart showing relative PD-L1 mRNA expression levels in 4T1 tumors from mice treated with dapansutrile compared to vehicle. $^{*}p<0.05$ (n=8, two independent experiments). FIG. 3E depicts a chart showing relative PD-L1 mRNA expression in vitro using murine triple-negative breast cancer cells (E0771). The E0771 cells were stimulated with IL-la and treated with vehicle or dapansutrile at the indicated concentrations. $^{*}p<0.05$ (n=3).

FIG. 4A depicts a schematic overview of experimental design. FIG. 4B depicts a chart quantifying IL-22 levels in splenocytes of mice treated with dapansutrile (OLT1177®), anti-PD-1, both anti-PD-1 and dapansutrile, or vehicle. FIG. 4B (vehicle vs. dapansutrile, p=0.037; vehicle vs. dapansutrile+anti-PD-1, p=0.048). FIG. 4C depicts a chart quantifying INFγ levels in splenocytes of mice treated dapansutrile, anti-PD-1, both anti-PD-1 and dapansutrile, or vehicle. FIG. 4C (vehicle vs. dapansutrile, p=0.044; vehicle vs. dapansutrile+anti-PD-1, p=0.022) (n=5).

DETAILED DESCRIPTION

Figure 1A:
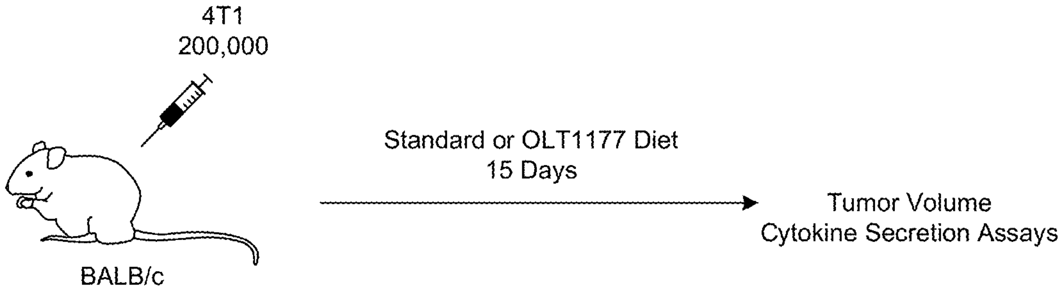
FIGS. 1A-1D.

Activation of the NLRP3 inflammasome amplifies the inflammatory response to tissue injury and mediates further damage. Dapansutrile is a selective NLRP3 inflammasome inhibitor; dapansutrile reduces inflammation by preventing activation of the NLRP3 inflammasome. Dapansutrile inhibits the production of mature IL-1β and IL-18 in mice and in human cells in vitro. Through this mechanism of action, dapansutrile prevents production and/or release of IL-1β and inhibits the formation of NLRP3 inflammasome in animals and human subjects.

The present invention is directed to a method of treating breast cancer, by administering an effective amount of dapansutrile to a subject. By inhibiting IL-1β, a main driver of breast tumor progression, dapansutrile reduces tumor volume and/or prevents tumor from further growth.

Compound

The present invention uses purified dapansutrile (3-methanesulfonyl-propionitrile), or the pharmaceutically acceptable salts or solvate thereof.

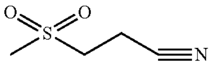

Dapansutrile

"Pharmaceutically acceptable salts," as used herein, are salts that retain the desired biological activity of the parent compound and do not impart undesired toxicological effects.

"Pharmaceutically acceptable solvates," as used herein, are solvates that retain the desired biological activity of the parent compound and do not impart undesired toxicological effects. "Solvates," as used herein, are addition complexes in which the compound is combined with an acceptable co-solvent in some fixed proportion. Co-solvents include, but are not limited to, water, acetic acid, ethanol, and other appropriate organic solvents.

Pharmaceutical Compositions

The active compound dapansutrile, or its pharmaceutically acceptable salt or solvate in the pharmaceutical compositions in general is in an amount of about 0.1-5% for an injectable formulation, about 1-90% for a tablet formulation, 1-100% for a capsule formulation, about 0.01-20%, 0.05-20%, 0.1-20%, 0.2-15%, 0.5-10%, or 1-5% (w/w) for a topical formulation, and about 0.1-5% for a patch formulation.

"About" as used in this application, refers to ±10% of the recited value.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of dapansutrile may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of dapansutrile may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

Topical formulations including dapansutrile can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent). In one embodiment, diethylene glycol monoethylether is included in the topical gel formulation.

Method of Use

By inhibiting assembly of the NLRP3 inflammasome, dapansutrile prevents the production and/or release of proinflammatory cytokines IL-1β and IL-22, and ultimately treating breast cancer tumor growth.

The present invention is directed to a method of treating breast cancer. The method comprises a step of administering to a subject in need thereof an effective amount of dapansutrile. "An effective amount," as used herein, is the amount effective to treat a disease by ameliorating the pathological condition, and/or reducing, improving, and/or eliminating the symptoms of the disease. For example, an effective amount is an amount that reduces the growth of breast cancer, and/or reduces the breast tumor size.

Breast cancer suitable to be treated by the present method includes triple negative breast cancer (TNBC), ductal carcinoma in situ (DCIS), invasive ductal carcinoma (IDC), inflammatory breast cancer (IBC), metastatic breast cancer, and breast cancer during pregnancy, among other types.

Checkpoint inhibitor therapy is a form of cancer immunotherapy. The therapy targets immune checkpoints, key regulators of the immune system that when stimulated can dampen the immune response to an immunologic stimulus. Some cancers can protect themselves from attack by stimulating immune checkpoint targets.

Immunotherapy has significantly improved the standard of care for breast cancer patients; however, non-responders and the number of relapsing patients are still high. Therefore, combination therapies that increase the efficacy of checkpoint inhibitors represent an important clinical benefit.

In one embodiment, the present invention is directed to a combination therapy by combining dapansutrile and a checkpoint inhibitor for treating breast cancer. The method comprises administering an effective amount of dapansutrile and an effective amount of a checkpoint inhibitor to a subject in need thereof. Dapansutrile and a checkpoint inhibitor can be administered simultaneously or sequentially. It is advantageous to co-administer dapansutrile with a checkpoint inhibitor because dapansutrile may improve the efficacy of a checkpoint inhibitor and dapansutrile has a safe drug profile. The co-administration may also reduce the required dosage of the checkpoint inhibitor, which reduces immunotherapy-related adverse events.

Checkpoint inhibitors suitable for use with dapansutrile for treating breast cancer include cytotoxic T lymphocyte associated protein 4 (CTLA-4), programmed cell death protein 1 (PD-1), and programmed death ligand 1 (PD-L1).

PD-1 is found on the surface of T cells and is the receptor for PD-L1. PD-1 plays a role in down-regulating immune responses by suppressing inflammatory T cell activity. This mechanism helps the body to prevent autoimmune diseases, however, the mechanism can also prevent the cancer cells from being killed (9).

In a preferred embodiment, the checkpoint inhibitor is an anti-PD-1 antibody. The method comprises administering an effective amount of dapansutrile and an effective amount of anti-PD-1 antibody to a subject in need thereof. Dapansutrile and anti-PD-1 antibody can be administered simultaneously or sequentially. It is advantageous to co-administer dapansutrile with anti-PD-1 antibody because dapansutrile improves the efficacy of anti-PD-1 and dapansutrile has a safe drug profile. The co-administration may also reduce the required dosage of anti-PD-1 antibody, which reduces immunotherapy-related adverse events.

The inventors have demonstrated that dapansutrile treatment reduces tumor growth of 4T1 TNBC in mice compared to vehicle.

Moreover, the inventors have demonstrated that dapansutrile reduces tumor promoting IL-22 and increases INFγ in splenocytes of treated mice.

The pharmaceutical composition of the present invention can be applied by systemic administration or local administration. Systemic administration includes, but is not limited to oral, parenteral (such as intravenous, intramuscular, subcutaneous or rectal), and inhaled administration. In systemic administration, the active compound first reaches plasma and then distributes into target tissues. Oral administration is a preferred route of administration for the present invention. Local administration includes topical administration.

Dosing of the composition can vary based on the extent of the subject's breast cancer and each patient's individual response. For systemic administration, plasma concentrations of the active compound delivered can vary; but are generally $1\times10^{10}$-$1\times10^{-4}$ moles/liter, and preferably $1\times10^{-8}$-$1\times10^{-5}$ moles/liter.

In one embodiment, the pharmaceutical composition is administrated orally to a subject. The dosage for oral administration is generally at least 1 mg/kg/day and less than 100 mg/kg/day, preferably 5-100 mg/kg/day, depending on the subject's age and condition. For example, the dosage for oral administration is 1-10, or 1-50, or 1-100, or 5-50, or 5-100, or 10-50, or 10-100 mg/kg/day for a human subject. For example, the dosage for oral administration is 100-10,000 mg/day, and preferably 100-2500, 500-2500, 500-4000, 1000-5000, 2000-5000, 2000-6000, or 2000-8000 mg/day for a human subject. The drug can be orally taken once, twice, three times, or four times a day. The patient is treated daily for 14 days up to 1 month, 2 months, or 3 months or for lifespan.

In one embodiment, the pharmaceutical composition is administrated intravenously to a subject. The dosage for intravenous bolus injection or intravenous infusion is generally 0.03 to 5 or 0.03 to 1 mg/kg/day.

In one embodiment, the pharmaceutical composition is administrated subcutaneously to the subject. The dosage for subcutaneous administration is generally 0.3-20, 0.3-3, or 0.1-1 mg/kg/day.

In one embodiment, the composition is applied topically. The composition is topically applied at least 1 or 2 times a day, or 3 to 4 times per day, depending on the medical issue and the disease pathology. In general, the topical composition comprises about 0.01-20%, or 0.05-20%, or 0.1-20%, or 0.2-15%, 0.5-10, or 1-5% (w/w) of the active compound. Typically, 0.2-10 mL of the topical composition is applied to the individual per dose.

Those of skill in the art will recognize that a wide variety of delivery mechanisms are also suitable for the present invention.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

EXAMPLES

The following materials and protocols were used in the examples described below.

Cell Lines. The mammary carcinoma cell lines 4T1, E0771, and MDA-468 were obtained from ATCC (Manassas, VA). Cells were cultured in DMEM supplemented with 10% FBS, 100 units/mL penicillin, 0.1 mg/ml streptomycin. Cells were maintained in a humidified 5% $CO_2$ atmosphere at 37° C.

In vitro. Tumor cell lines were adhered overnight at a concentration of 200,000 per well. The following day human recombinant IL-1α or IL-1β (R&D Systems, Minneapolis, MN) were added with or without dapansutrile (OLT1177®) and incubated for 24 hours. Cells were then lysed using TRIzol reagent (Thermo Fisher Scientific, Waltham, MA).

Gene Expression. RNA was then isolated using Trizol (Thermo Fisher Scientific) and synthesized in cDNA using SuperScript III First-Strand (Thermo Fisher Scientific). Quantitative PCR (qPCR) was performed on cDNA using Power SYBR Green PCR master mix (Thermo Fisher Scientific) on Biorad CFX96 Real time system. Gene expression was assessed for Tslp, Tslpr, and Pdcd-11L1 mRNAs as indicated using the following primers:

```
Tslp forward,
                                        (SEQ ID NO: 1)
5'-TACTCTCAATCCTATCCCTGGCTG-3';

Tslp reverse,
                                        (SEQ ID NO: 2)
5'-TGTGAGGTTTGATTCAGGCAGATG-3';

Tslpr forward,
                                        (SEQ ID NO: 3)
5'-TGACGTCACGGGGTGATGTC-3';

Tslpr reverse,
                                        (SEQ ID NO: 4)
5'-GAGGATGCACCCGGAAGTGA-3';

Pdcd1L1 forward,
                                        (SEQ ID NO: 5)
5'-GCTCCAAAGGACTTGTACGTG3';

Pdcd1L1 reverse,
                                        (SEQ ID NO: 6)
5'-TGATCTGAAGGGCAGCATTTC3'.
```

Tumor Model. Animal protocols were approved by the University of Colorado Health Sciences Center Animal Care and Use Committee. Female BALB/c mice, 6-8 weeks old (The Jackson Laboratory), were fed standard or dapansutrile (OLT1177®) diet (4), which was started on the day of 4T1 injection. 4T1 cells ($2\times10^5$) were injected orthotopically into the mammary fat pad. Mice treated with dapansutrile were fed ad libidum with food pellets containing 7.5 g/kg dapansutrile, which started on the day of the 4T1 injection and continued for 15 days. Mice typically consume about 4 g of food per day, resulting in an approximate daily dose of 0 mg/kg/day for control groups and 1,000 mg/kg/day for the treatment groups. This food pellet concentration (7.5 g/kg of dapansutrile in food) in mouse chow resulted in a blood level nearly the same as that of humans treated orally with dapansutrile at doses of 1000 mg/day (40 μg/mL blood level) (14). Control ("vehicle") mice were fed with control food pellets without dapansutrile. Mice were sacrificed following 15 days after 4T1 injection.

Anti-PD-1 Combination Therapy. 4T1 cells were injected as described. After instillation of 4T1 cells, mice were started on dapansutrile (OLT1177®) diet or continued on standard diet as described and at day seven a neutralizing antibody against PD-1 (200 μg/mouse; BioXCell, West Lebanon, NH) was injected peritoneally. Mice were sacrificed following 15 days from the B16F10 instillation.

Anti-IL-1α Combination Therapy. 4T1 cells were injected as described. After instillation of 4T1 cells, mice were started on dapansutrile (OLT1177®) diet or continued on standard diet as described and every three days a neutralizing antibody against anti-IL-1α (200 μg/mouse; XBioTech, Austin, TX) was injected peritoneally. Mice were sacrificed following 15 days from the B16F10 instillation.

Splenocyte Cytokine Secretion. 4T1 cells were injected as described. Spleens from tumor-bearing mice were processed for cell culture through mechanical dissociation. Cells suspended in RPMI supplemented with 10% FBS, 100 units/mL penicillin, 0.1 mg/ml streptomycin and were plated at 5.0e^5 and stimulated with 10 μg/mL LPS. After 72 hours, supernatants were removed and cytokines were measured via ELISA (R&D Systems, Minneapolis, MN).

Example 1: Dapansutrile Reduces Breast Tumor Volume in 4T1 TNBC Mice

In this Example, inventors assessed whether an oral NLRP3 inhibitor, dapansutrile, was effective in reducing tumor growth in a murine 4T1 TNBC model.

Figure 1B:
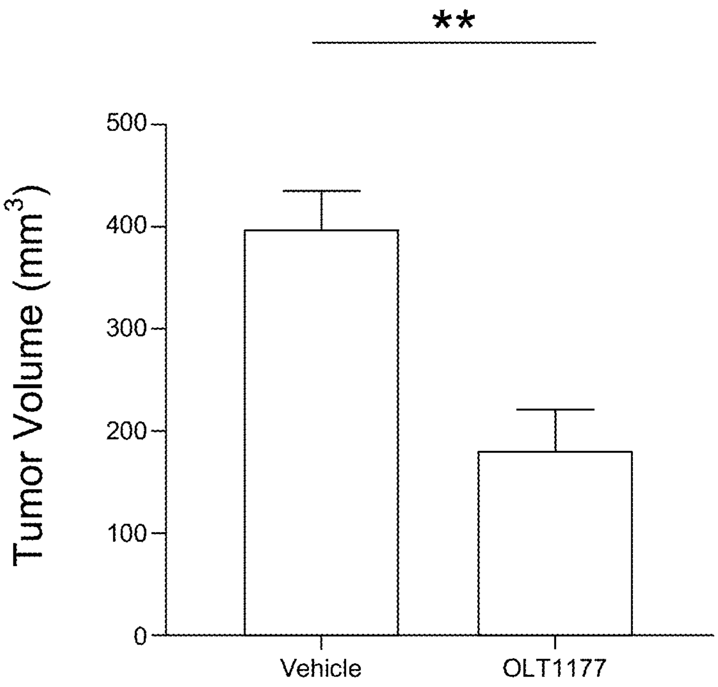
Figure 1C:
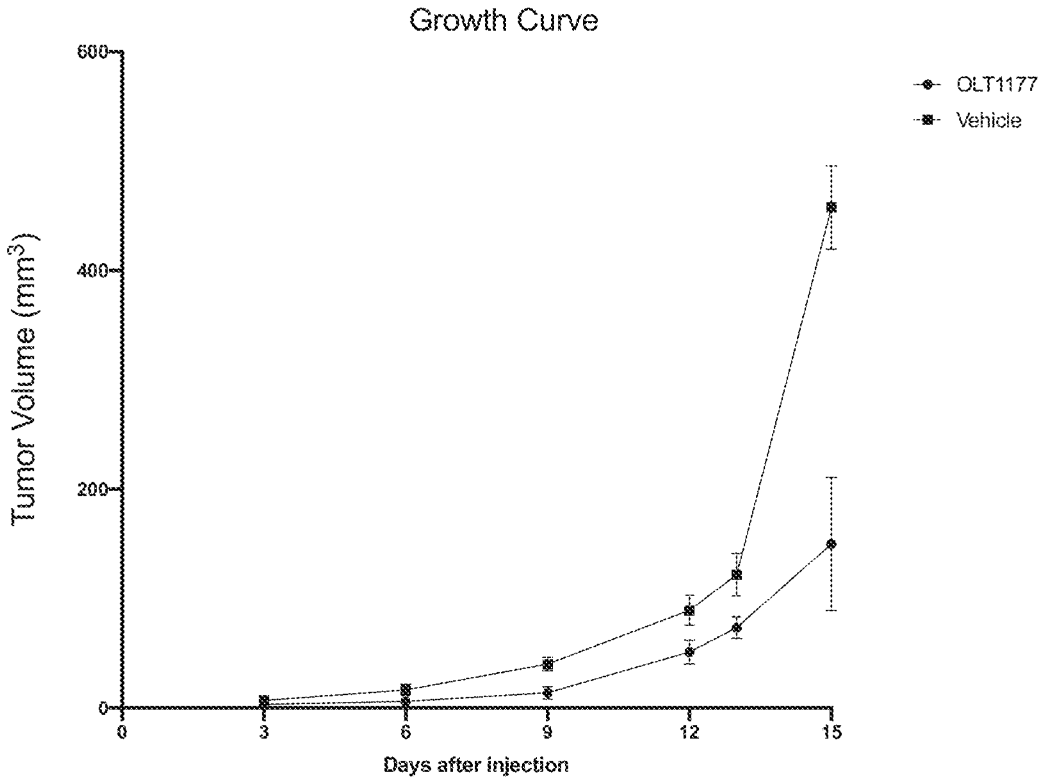
Figure 1D:
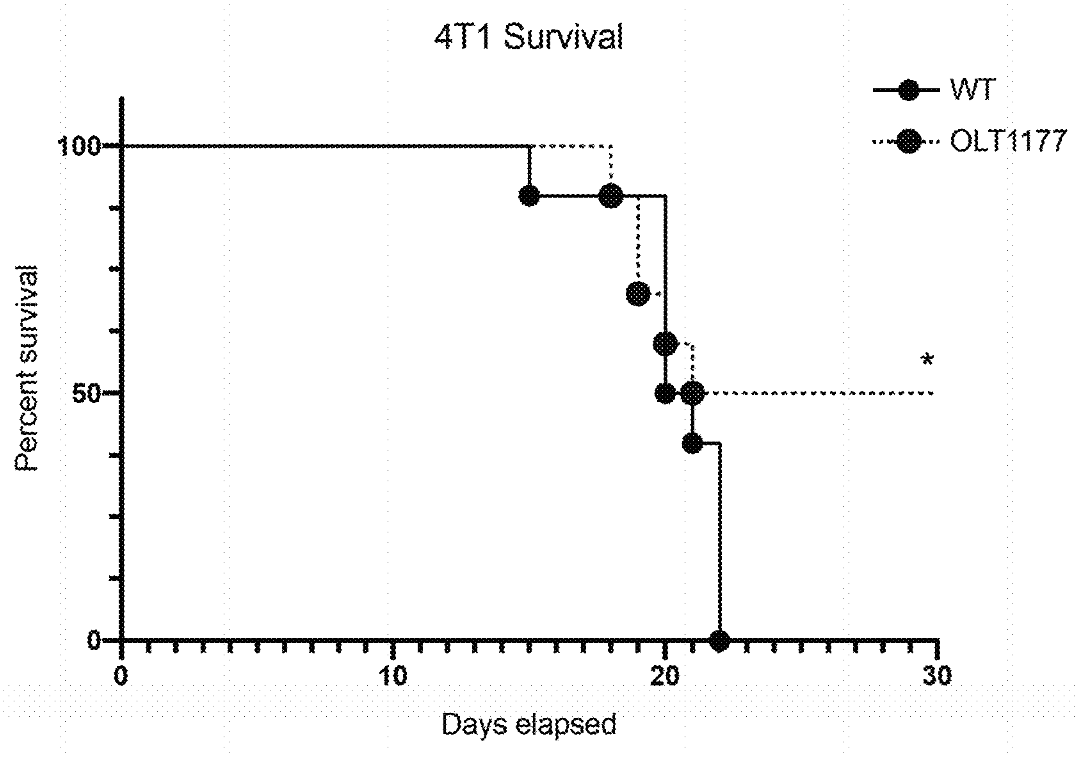

4T1 TNBC mice were generated and fed a standard diet or a dapansutrile diet for 15 days. Tumors were measured on indicated days to generate a growth curve (FIG. 1C). Final tumor volume was taken following resection of the tumors (FIG. 1B). Tumor-bearing mice fed a dapansutrile diet showed significantly decreased tumor volume (FIG. 1B, $^{}p<0.01$). In survival studies, 4T1 TNBC mice treated with dapansutrile showed significantly higher survival rates compared to mice on standard diet (FIG. 1**D, n=10, $^{*}p<0.05$) with half of the mice on dapansutrile diet surviving beyond 30 days.

In these experiments, mice treated with dapansutrile showed significant tumor volume reduction compared to vehicle controls. Collectively, FIGS. 1A-1D show that dapansutrile reduced tumor volume and resulted in significantly higher survival rates in a mouse model for triple-negative breast cancer (4T1 TNBC mice).

Example 2: Dapansutrile Reduces Breast Tumor Volume Alone and when Co-Administered with Anti-IL-1α

Figure 2A:
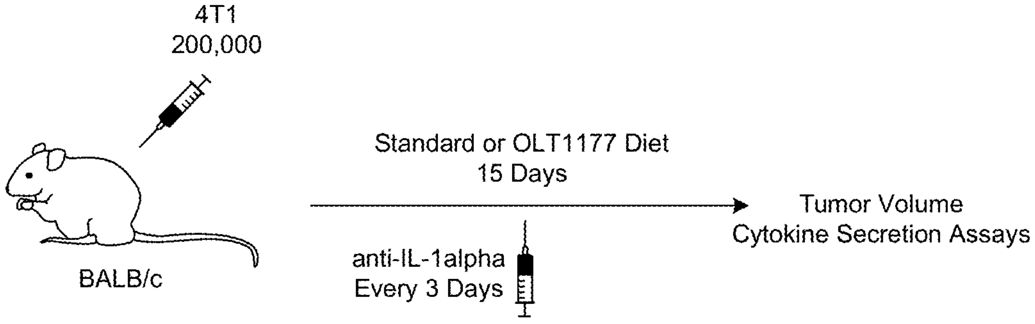
FIGS. 2A-2G.
Figure 2B:
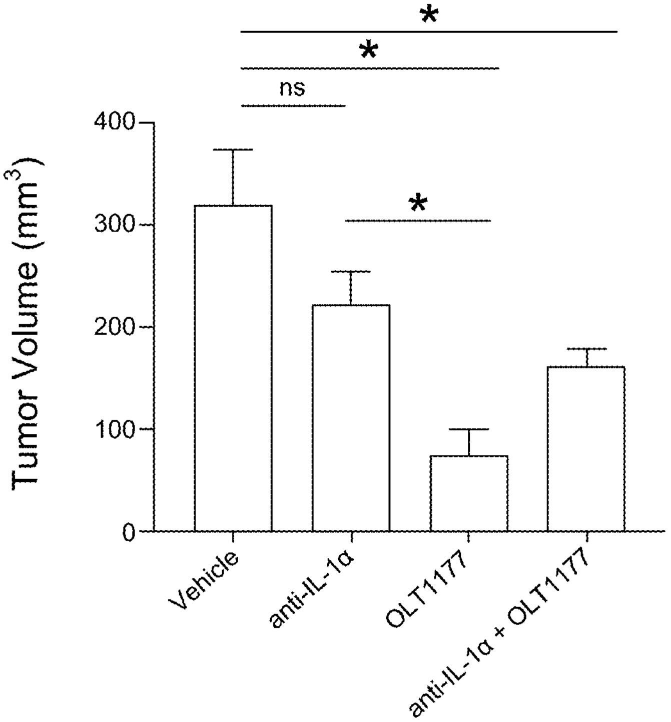
Figure 2C:
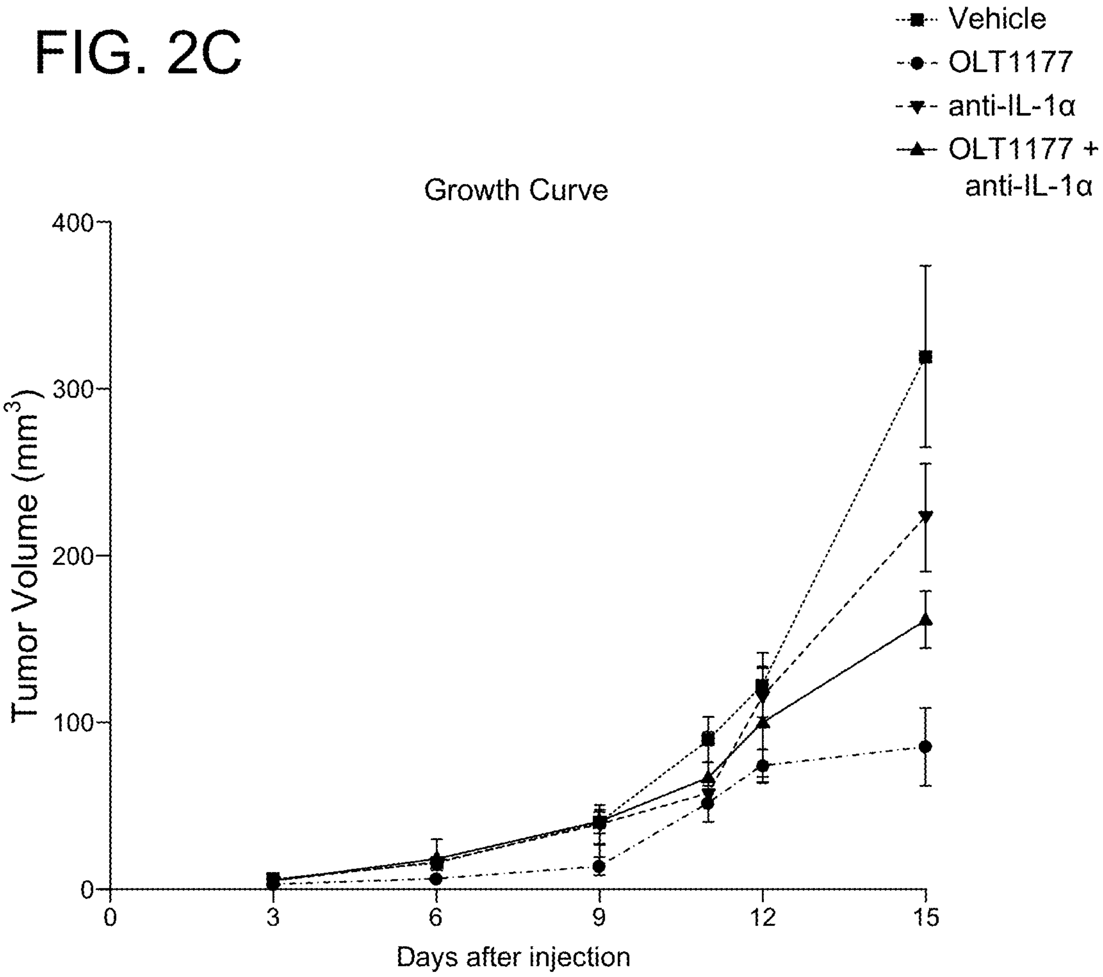

Previous studies indicate that $HER2^-$ metastatic breast cancer patients receiving IL1R antagonist anakinra treatment downregulated components of the inflammatory signature seen in metastatic breast cancer patients (10). To further assess the roles of IL-1α and IL-1β in driving 4T1 tumor progression, inventors treated mice with anti-IL-1α (200 μg/mouse), dapansutrile diet, and a combination of both. 4T1 TNBC mice were generated and fed a standard diet or a dapansutrile diet for 15 days. Mice were injected with anti-IL1α every 3 days as indicated. Subsequently, tumor volume was analyzed. FIGS. 2B and 2C show significantly reduced tumor volumes ($^{*}p<0.05$) for tumor-bearing mice treated with a dapansutrile diet alone and in combination with IL-1α when compared to vehicle.

In these experiments, mice treated with dapansutrile was effective in reducing tumor volumes, whereas anti-IL-1α monotherapy did not significantly reduce tumor volumes. Together these data suggest that IL-1β may have stronger tumor-promoting effects than IL-1α in 4T1 TNBC.

Figure 2D:
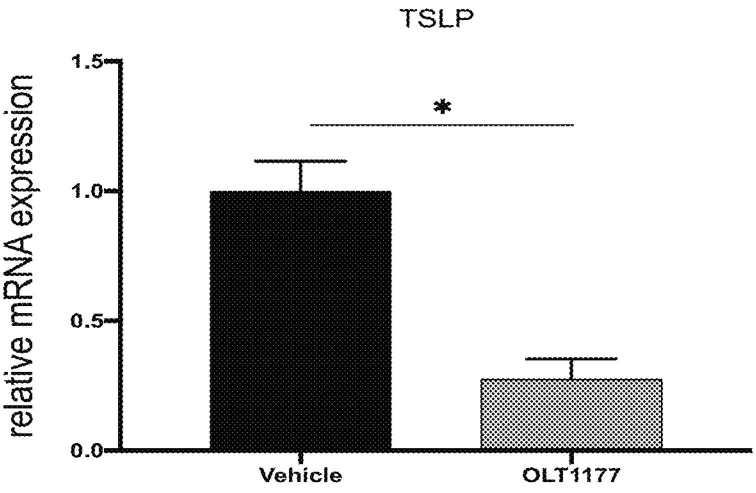
Figure 2E:
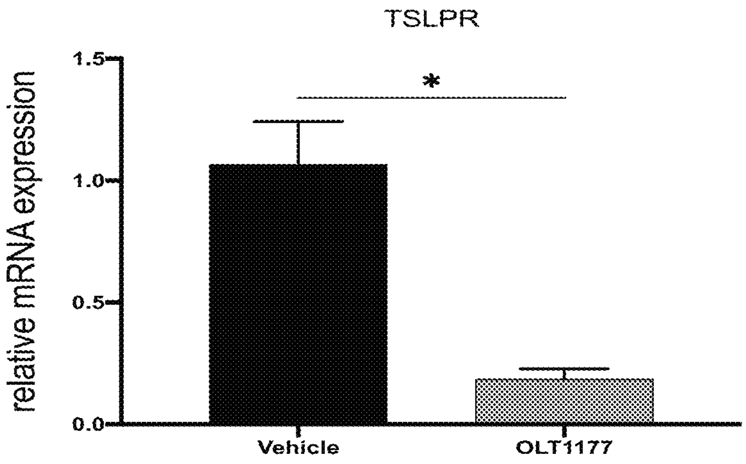
Figure 2F:
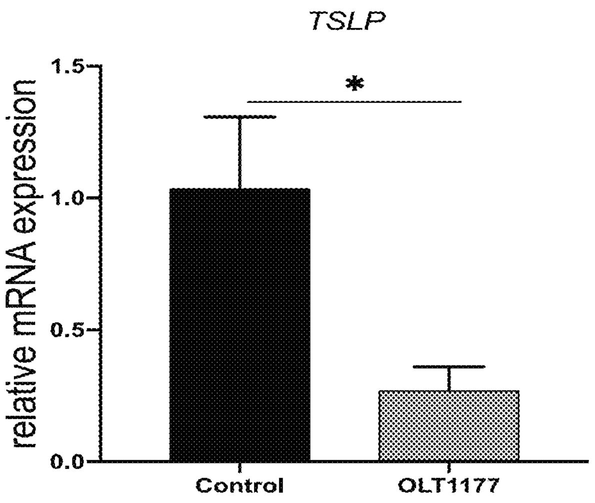
Figure 2G:
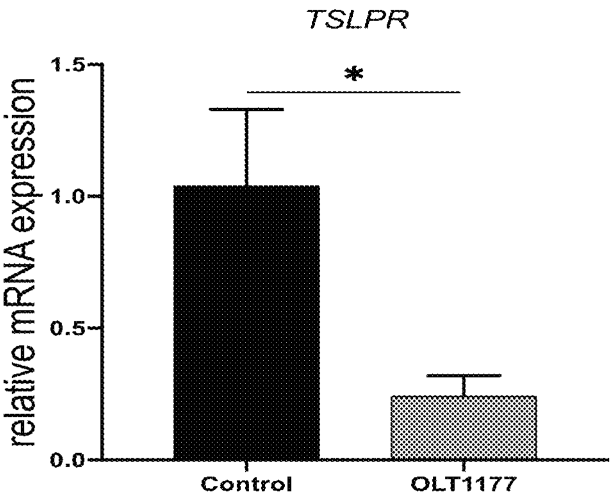

Previous studies on the tumor-myeloid cell interactions in triple-negative breast cancer indicate that tumor-derived IL-1α promotes infiltrating myeloid cells to secrete TSLP (thymic stromal lymphopoietin), which in turn is critical for tumor progression at both primary and distant metastatic sites (15). To further evaluate the effects of blocking NLRP3 in 4T1 tumor progression, inventors quantified gene expression of TSLP and its associated receptor TSLPR in primary 4T1 tumors as measured by relative mRNA expression. FIGS. 2D and 2E show significantly lower TSLP and TSLPR expression ($^{*}p<0.05$) in tumor-bearing mice treated with a dapansutrile diet compared to vehicle. This analysis was performed on the same mice as in FIGS. 2B and 2C. To confirm these findings in vitro, inventors used the human TNBC cell line MDA-468. MDA-468 cells were stimulated with IL-1α (20 ng/mL) and incubated with dapansutrile (10 μM) or without dapansutrile (control) for 24 hours. FIGS. 2F and 2G show significantly lower TSLP and TSLPR expression (*$p<0.05$) compared to controls. These findings demonstrate that both IL-1α and IL-1β promote TSLP/TSLPR and that the pathway is both tumor-intrinsic and tumor-myeloid.

Example 3: Dapansutrile Reduces Breast Tumor Volume Alone and when Co-Administered with Anti-PD-1

In this Example, inventors investigated the tumor reducing effects of dapansutrile and anti-PD-1.

Figure 3A:
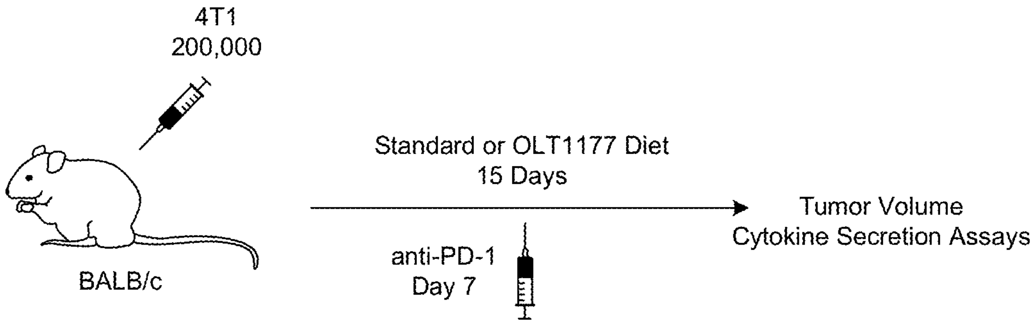
FIGS. 3A-3E.

4T1 TNBC mice were generated and fed a standard diet or a dapansutrile diet for 15 days. Mice receiving a combination therapy were injected with anti-PD-1 on day 7 as indicated (FIG. 3A).

Figure 3B:
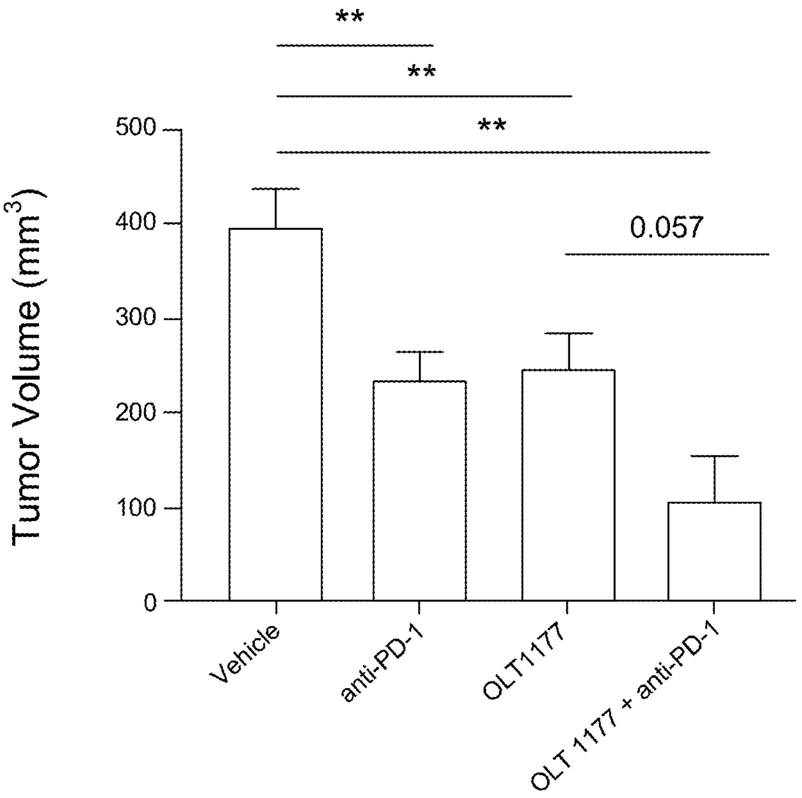
Figure 3C:
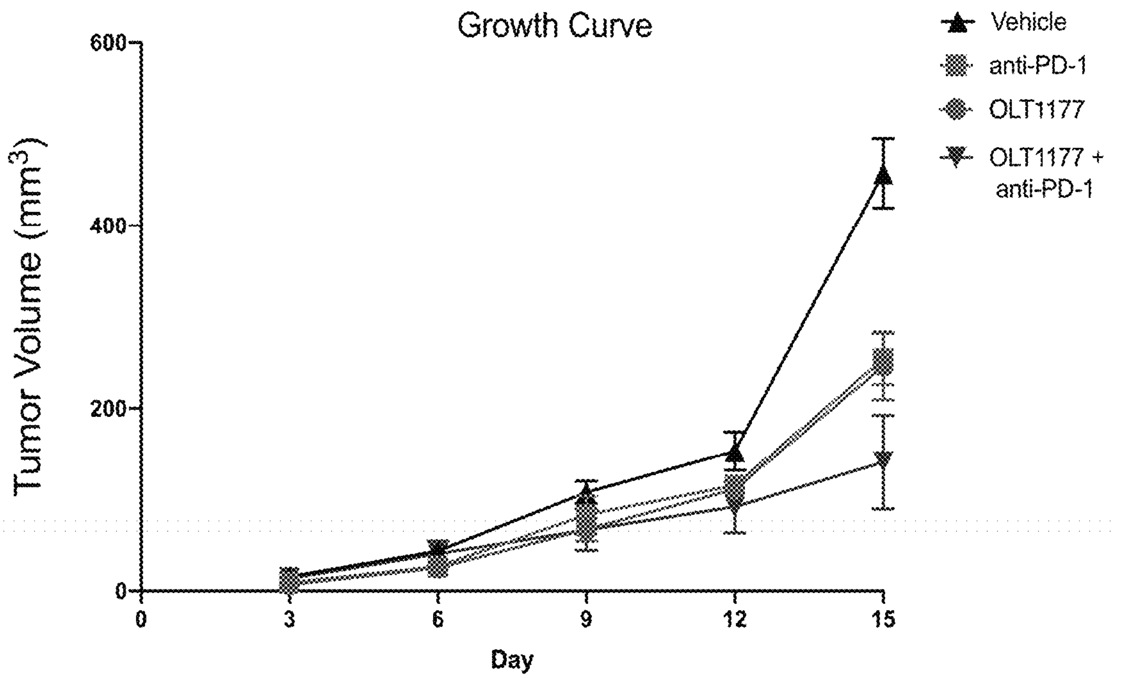

The results are shown in FIGS. 3B and 3C. Tumor volume measurements were taken from tumors on mice in vivo on the days indicated in FIG. 3C. Following sacrifice on day 15, tumors were removed and tumor volume measured as shown in FIG. 3B. Tumor-bearing mice treated with dapansutrile monotherapy showed a significant tumor reduction compared to vehicle ($p=0.0041$). Mice receiving anti-PD-1 alone also showed a significant tumor reduction ($p=0.0069$). Mice receiving the combination of dapansutrile and anti-PD- showed an even more significant tumor reduction (**$p=0.0014$).

To examine the effects of dapansutrile on PD-L1 gene expression levels, further in vivo analysis was conducted on tumors from 4T1 TNBC mice from FIGS. 2B and 2C.

Figure 3D:
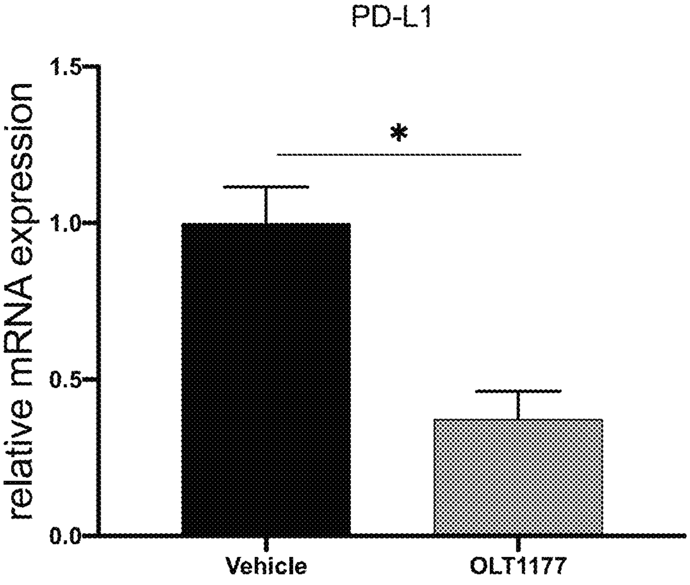

Results are shown in FIG. 3D. 4T1 tumors from mice fed a dapansutrile diet expressed significantly less PD-L1 gene expression than mice fed a standard diet as quantified by relative mRNA expression. FIG. 3D (*$p<0.05$; n=8, two independent experiments). This finding suggests a possible mechanism for the enhanced effect of anti-PD-1 therapy.

In vitro analysis of the murine triple-negative breast cancer cell line E0771 was conducted to examine the effects of dapansutrile on PD-L1 expression levels following cell death signaling. IL-1α stimulation was used to simulate cell death signaling in the tumor-microenvironment. Cells were stimulated with IL-1α at 10 ng/mL and treated with dapansutrile at the indicated concentration or untreated (vehicle).

Figure 3E:
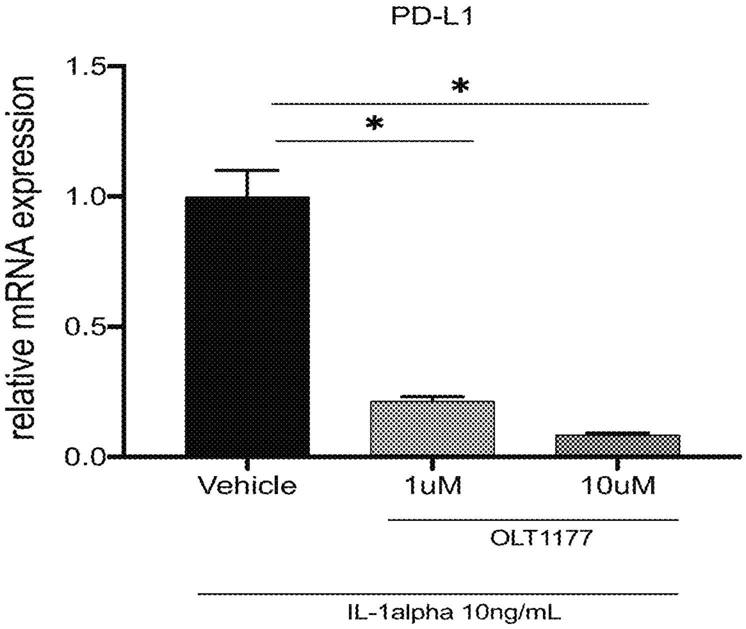

Results are shown in FIG. 3E. E0771 cells treated with dapansutrile after IL-1α stimulation express markedly lower PD-L1 (*$p<0.05$) (n=3).

Example 4: Dapansutrile Reduces IL-22 and Increases INFγ in Splenocytes

Recent insight into the cytokine IL-22 has revealed a tumor-promoting role in breast cancer in that it recruits immunosuppressive cells to the tumor-microenvironment (11). Experiments were performed here to examine cytokine production in spleens from tumor-bearing mice after monotherapy of dapansutrile and anti-PD-1, and also in combination.

Figure 4A:
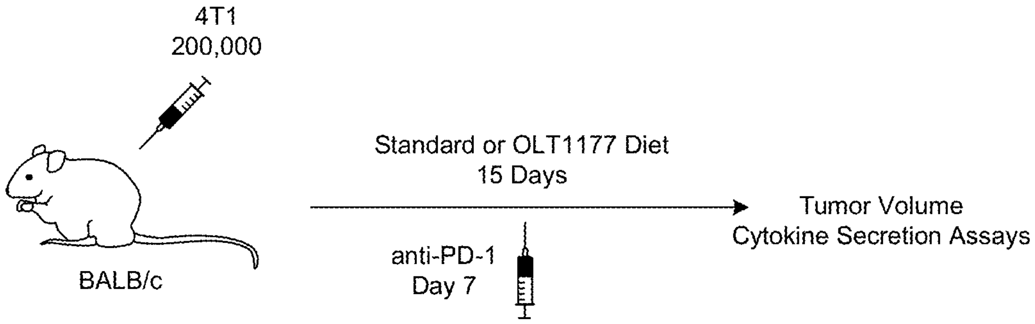
FIGS. 4A-4C.

In this Example, 4T1 TNBC mice were generated and fed a standard diet or a dapansutrile diet for 15 days. Mice were injected with anti-PD-1 in a combination study on day 7 as indicated in FIG. 4A.

Figure 4B:
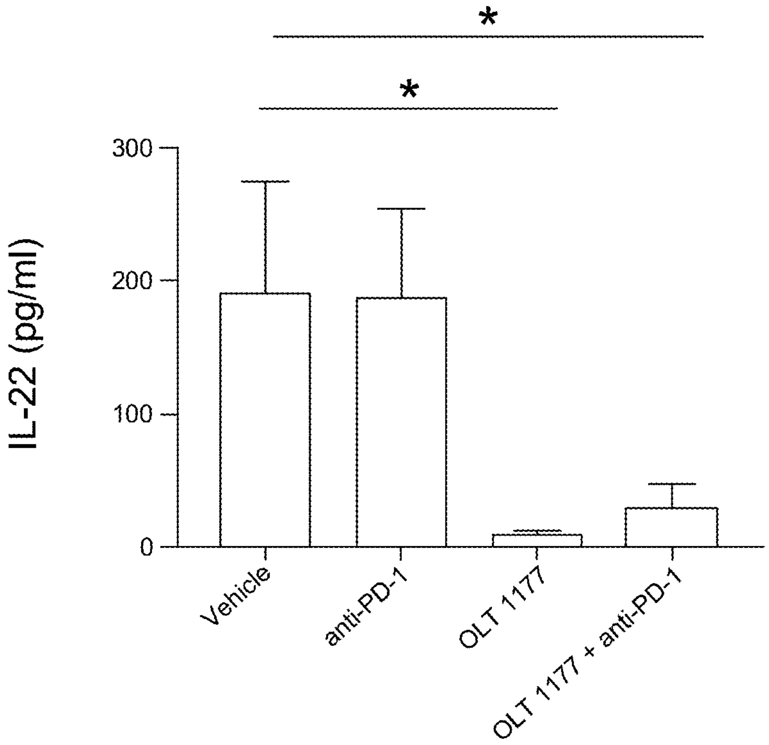
Figure 4C:
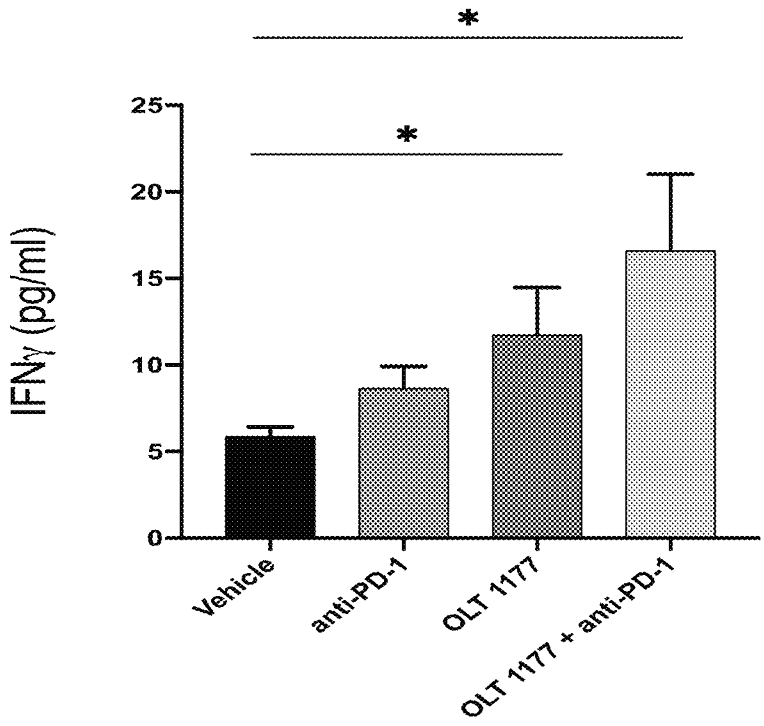

In these experiments, treatment with a dapansutrile monotherapy and a combination therapy with anti-PD-1 significantly reduced IL-22 levels (*$p<0.05$). However, treatment with anti-PD-1 alone failed to reduce IL-22 levels compared to vehicle. See FIG. 4B. These data suggest that IL-1β induction of IL-22 was ultimately suppressed in dapansutrile feed mice. The results also show that IFNγ levels increased in the dapansutrile and combination groups, which suggests increased tumoricidal NK cell activity (*$p<0.05$). See FIG. 4C.

REFERENCES

1. Y. Guo, et al. Cancer Res 77, 6429-6441 (2017).
2. S. Shalapour, et al. J Clin Invest 125, 3347-3355 (2015).
3. C. A. Dinarello. Blood 117, 3720-3732 (2011).
4. R. N. Apte, et al. Cancer Metastasis Rev 25, 387-408 (2006).
5. C. A. Dinarello. Cancer Metastasis Rev 29, 317-329 (2010).
6. B. Guo, et al. Sci Rep 6, 36107 (2016).
7. K. L. Lee, et al. Cancers 11(9), 1334 (2019).
8. C. Marchetti, et al. Proc Natl Acad Sci USA 115, E1530-E1539 (2018).
9. N. L. Syn, et al. Lancet Oncology 18(12), PE731-E741 (2017).
10. T. C. Wu, et al., Cancer Res 78(18):5243-5258 (2018).
11. C. Voigt, et al. Proc Natl Acad Sci USA 114:12994-12999 (2017).
12. P. M. Ridker et al. Lancet 390(10105):1833-1842 (2017).
13. I. Kaplanov, et al. Proc Natl Acad Sci USA 116(4):1361-1369 (2019).
14. C. Marchetti, et al. Arthritis Res Ther 20:169 (2018).
15. E. L. Kuan, et al. Nat Immunol 19, 366-374 (2018).

From the foregoing, it will be appreciated that specific embodiments of the invention have been described herein for purposes of illustration, but that various modifications may be made without deviating from the scope of the invention. Accordingly, the invention is not limited by the appended claims.

What is claimed is:

1. A method of treating breast cancer in a subject, comprising the step of:

administering to a subject in need thereof an effective amount of dapansutrile, or a pharmaceutically acceptable solvate thereof, wherein dapansutrile is administered by oral administration in an amount of 500-4000 mg/day.

2. The method according to claim 1, wherein the breast cancer is selected from the group consisting of: ductal carcinoma in situ (DCIS), invasive ductal carcinoma (IDC), triple negative breast cancer (TNBC), inflammatory breast cancer (IBC), metastatic breast cancer, and breast cancer during pregnancy.

3. The method according to claim 1, wherein the method reduces the size of the breast tumor.

4. The method according to claim 1, wherein the method reduces further growth of the breast tumor.

5. The method according to claim 1, further comprising administering to the subject an effective amount of a checkpoint inhibitor.

6. The method according to claim 5, wherein the checkpoint inhibitor is an anti-PD-1 antibody.

7. The method according to claim 1, wherein the breast cancer is triple negative breast cancer.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
```

-continued

```
tactctcaat cctatccctg gctg                                              24


<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2

tgtgaggttt gattcaggca gatg                                              24


<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3

tgacgtcacg gggtgatgtc                                                   20


<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4

gaggatgcac ccggaagtga                                                   20


<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5

gctccaaagg acttgtacgt g                                                 21


<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6

tgatctgaag ggcagcattt c                                                 21
```